(12) United States Patent
Eden

(10) Patent No.: US 6,710,347 B1
(45) Date of Patent: Mar. 23, 2004

(54) DEVICE FOR MEASURING GAS CONCENTRATION

(75) Inventor: Gideon Eden, Ann Arbor, MI (US)

(73) Assignee: Sensors, Inc., Saline, MI (US)

( * ) Notice: Subject to any disclaimer, the term of this patent is extended or adjusted under 35 U.S.C. 154(b) by 0 days.

(21) Appl. No.: 10/096,227

(22) Filed: Mar. 12, 2002

(51) Int. Cl.[7] ................................. G01J 5/02
(52) U.S. Cl. ..................... 250/343; 250/336.1
(58) Field of Search ............... 250/343, 336.1, 250/338.1, 318, 436, 354.1, 339.04, 339.03, 339.13

(56) References Cited

U.S. PATENT DOCUMENTS

| | | | | |
|---|---|---|---|---|
| 3,732,017 A | * | 5/1973 | Wolber | 356/436 |
| 5,184,017 A | | 2/1993 | Tury et al. | 250/343 |
| 5,559,333 A | * | 9/1996 | Araya et al. | 250/344 |
| 5,886,348 A | * | 3/1999 | Lessure et al. | 250/339.13 |
| RE36,277 E | | 8/1999 | Black et al. | 250/339.13 |
| 2001/0045521 A1 | * | 11/2001 | Prozzo et al. | 250/345 |
| 2002/0050567 A1 | * | 5/2002 | Boudet et al. | 250/345 |

OTHER PUBLICATIONS

Commonly assigned co–pending U.S. application Ser. No. 09/911,836, filed Jul. 24, 2001, entitled Vehicle Emission Sampling and Analysis Assembly (SEN01 P–338A). Eden, Gideon.

* cited by examiner

Primary Examiner—David Porta
Assistant Examiner—Christine Sung
(74) Attorney, Agent, or Firm—Van Dyke, Gardner, Linn & Burkhart, LLP

(57) ABSTRACT

An apparatus and method for detecting at least one component gas in a sample includes a radiation source for providing radiation along an optical path in a pre-selected spectral band having at least one absorption line of the component gas to be detected and an optical detector for detecting radiation at the optical path. A sample chamber is positioned in the optical path between the source and the optical detector to contain a quantity of a sample gas. At least one gas cell enclosing an amount of the gas to be detected is fixedly positioned in the optical path in series with the gas chamber. A mathematical relationship is determined between the detected radiation and the concentration of a sample gas filling the sample chamber.

31 Claims, 2 Drawing Sheets

DEVICE FOR MEASURING GAS CONCENTRATION

BACKGROUND OF THE INVENTION

This invention relates to gas analyzers for determining the presence and concentrations of gas components in a sample. The invention is especially adapted for use in the area of environmental measurements, such as engine emissions, although it may have other applications.

Using gas cells for calibration of optical gas benches has been described in the prior art. U.S. Pat. No. 5,060,505 describes an infrared-based device to measure gas concentration in which gas cells enclosing an amount of the component gas to be detected are selectively positioned in the optical path. While this device is very effective in eliminating the necessity for utilizing gases for calibration, it requires mechanical means to place and remove the gas cell in the optical path. The required mechanical means cannot be effectively used for measuring gas emissions of moving vehicles since they are quite sensitive to vibration.

SUMMARY OF THE INVENTION

An apparatus for detecting at least one component gas in a sample includes a source for providing radiation along at least one optical path in a pre-selected spectral band. The spectral band has at least one absorption line of the component gas to be detected. The apparatus further includes at least one optical detector positioned in the at least one optical path for detecting radiation in the pre-selected spectral band and for producing at least one detection output. A sample chamber is positioned in the at least one optical path between the source and the at least one detector and adapted to contain a quantity of sample gas including the component gas to be detected. A gas cell enclosing an amount of component gas to be detected is permanently positioned in the at least one optical path in series with the sample chamber. A control includes an algorithm for determining a mathematical relationship between the at least one detector output and the concentration of a sample gas filling the sample chamber.

A method for detecting at least one component gas in a sample, according to an aspect of the invention, includes providing radiation along at least one optical path in a pre-selected spectral band. The spectral band has at least one absorption line of the component gas to be detected. The method further includes detecting radiation in the at least one optical path in the pre-selected spectral band. The method further includes positioning a sample chamber in the at least one optical path. The sample chamber is adapted to contain a quantity of sample gas including the component gas to be detected. The method further includes fixedly positioning at least one gas cell enclosing an amount of the component gas to be detected in the at least one optical path in series with the sample chamber. The method further includes determining a mathematical relationship between radiation detected in the at least one optical path and the concentration of a sample gas filling the sample chamber.

The major advantage of the present invention is that gas cell(s) can be permanently embedded in the optical paths of the device. Therefore, gas analyzers with no moving parts can be effectively implemented.

DESCRIPTION OF THE PREFERRED EMBODIMENT

Figure 1:
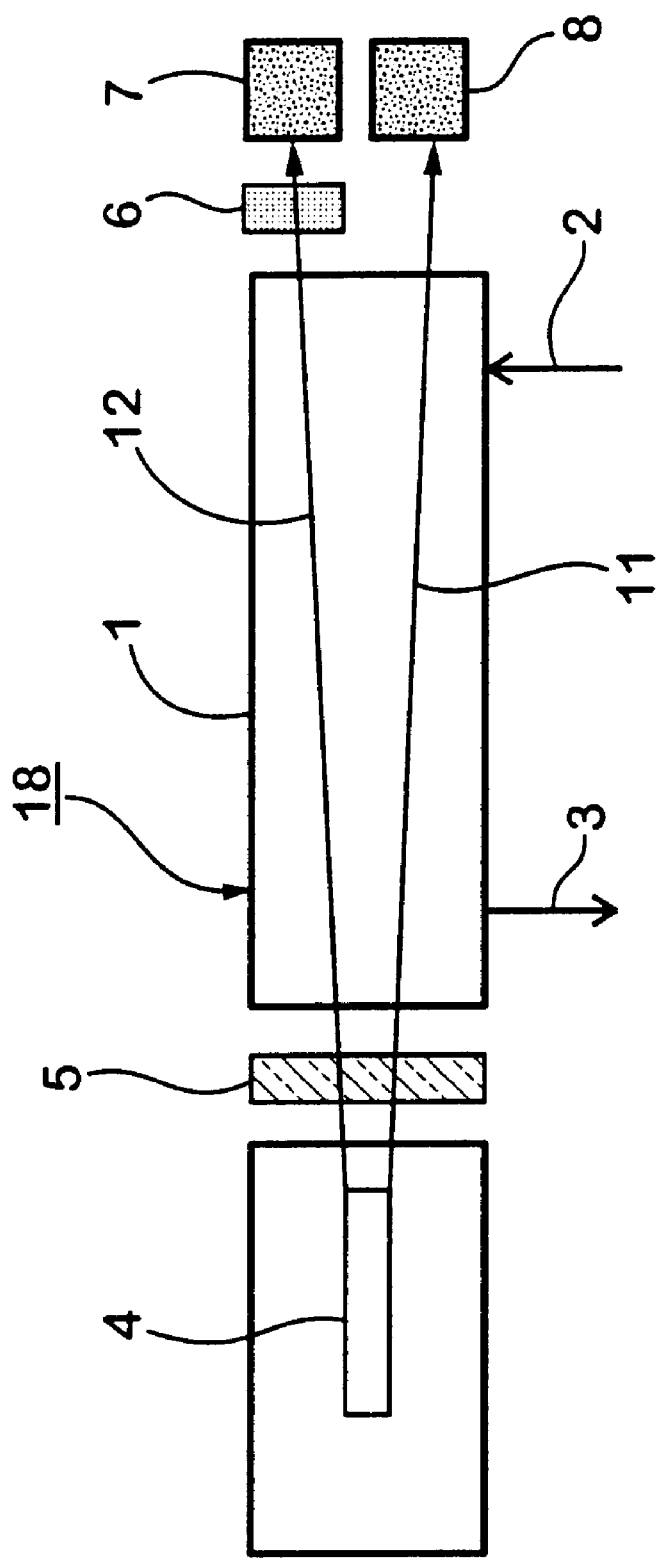
FIG. 1 is a diagram of an apparatus for detecting at least one component gas in a sample, according to the invention.

In the preferred embodiment, illustrated in FIG. 1, an apparatus 18 for detecting at least one component gas includes a gas-sampling cell 1. A sample gas is transferred through gas-sampling cell 1 through an inlet pipe 2 and exhausted through an outlet pipe 3 of gas-sampling cell 1. A radiation source 4 generates electromagnetic energy directed to the sample gas in the gas-sampling cell 1. The energy from the radiation source is preferably in the range of infrared, near infrared, visible or ultraviolet wavelengths. The emitted energy is limited to specific bands by an optical filter 5, such as an interference filter, which is well known in the art. These limited bands are chosen to cover certain absorption bands of at least one gas component present in the sample gas. The partially absorbed energy leaves the gas-sampling cell 1 through two optical channels 11 and 12. The gas channel 11 directs the energy to an optical detector 8, which measures the energy directly. Such detectors are well known in the art. The reference channel 12 directs the energy via a gas cell 6 to a second optical detector 7. The gas cell includes at least one gas component present in the sample gas that is being measured by the device. The gas cell is permanently present in the second channel thereby avoiding the necessity for additional mechanical components to selectively place and remove the gas cell to and from the channel.

Figure 2:
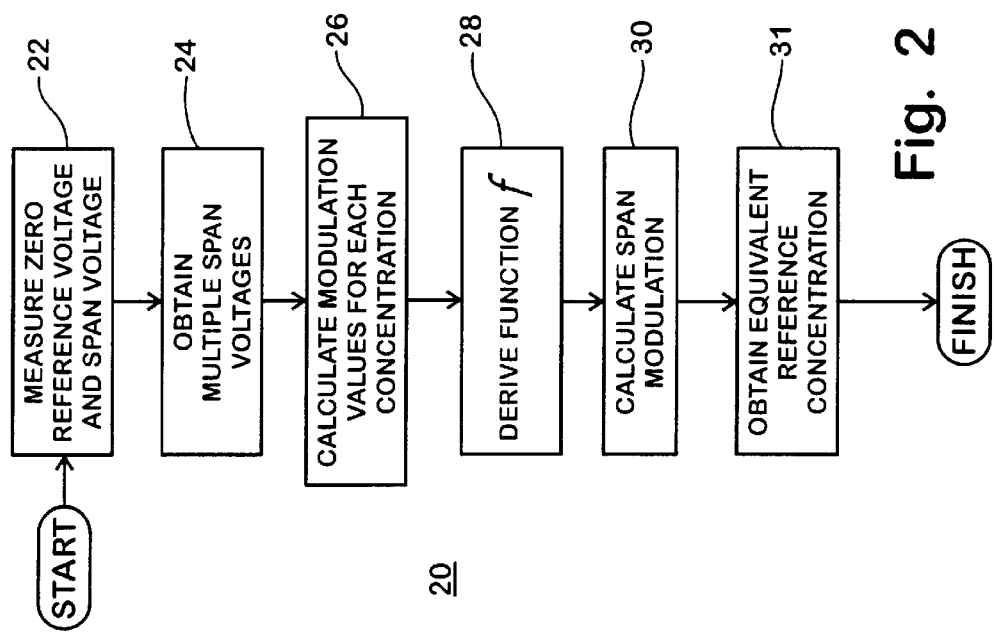
FIG. 2 is a flowchart of a calibration method, according to the invention.

The apparatus is calibrated using a calibration procedure 20, illustrated in FIG. 2. While calibration procedure 20 can be carried out at any time, it may, advantageously, be carried out during manufacturing of apparatus 18. Zero gas (nitrogen) is used at 22 to obtain and store the zero voltage $V_{zg}$ of the gas channel 11 measured by the detector 8, the zero reference voltage (gas cell out) $V_{zr}$ and the span voltage $V_r$ (gas cell in) in channel 12 as measured by the detector 7. Multiple gas concentrations are used at 24 to obtain the span voltage $V_i$ for each concentration $C_i$ in the gas channel 11. Modulation values $M_i$ for each concentration $C_i$ in the gas channel 11 are calculated at 26 using the expression:

$$M_i = (V_{zg} - V_i)/V_z$$

A function f (e.g., polynomial of $4^{th}$ order) is applied at 28. Function f relates the gas concentrations to the calculated modulation values according to:

$$C_i = f(M_i)$$

The reference span modulation obtained from the reference channel 12 is calculated and stored at 30 using:

$$M_r = (V_{zr} - V_r)/V_{zr}$$

An "equivalent reference concentration" $C_r$ may optionally be calculated and stored at 31 using:

$$C_r = f(M_r)$$

Figure 3:
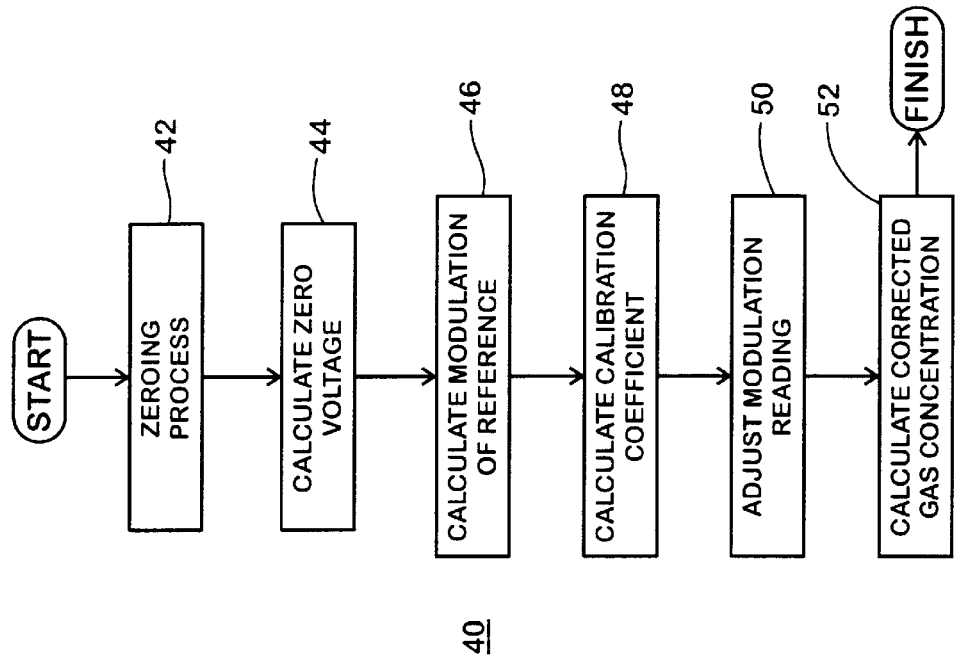
FIG. 3 is a flowchart of a method of detecting a component of a gas in a sample, according to the invention.

Once the apparatus is calibrated, the gas cell can be used in apparatus 18 instead of calibration gas stored in gas bottles using a component gas detection method 40, illustrated in FIG. 3. During the zeroing process 42, the zero gas channel voltage Vzg' is measured in channel 12 and the voltage of the reference channel Vr' is measured in channel 11. The zero voltage of the reference channel Vzr' is calculated at 44 by relating the zero voltage obtained in the manufacturing phase using:

$$Vzr'=(Vr'/Vr)Vzr$$

The modulation of the reference channel corresponding to the gas cell is calculated at 46 using:

$$Mr'=(Vzr'-Vr')/Vzr'$$

The Calibration Coefficient K is calculated at 48 using:

$$K=Mr'/Mr$$

Each modulation reading of the gas sample in the gas channel is adjusted at 50 by the Calibration Coefficient K:

$$Mg'=K*(Vzg'-Vg')/Vzg'$$

The corrected gas concentration is calculated at 52 by:

$$C=f(Mg')$$

Where f is the function determined in the manufacturing phase.

In a different embodiment of the invention, a sampling cell with a single optical path can be implemented. In this case, both the sampling cell and the gas cell are serially placed in the optical path between the radiation source and the optical detector. During manufacturing, two zero-voltage values are read and stored, one with the gas filter present in the optical path and the other without the gas cell, thereby providing a calibration reference based upon the gas concentration enclosed in the cell.

The radiation source generates electromagnetic energy in specific energy bands. It can cover the whole range utilized for spectroscopy; i.e., visible light, near infrared, infrared or ultraviolet radiation. Usually, heated filaments are used for the infrared and visible ranges. Gas discharge lamps can be used for the visible and the ultraviolet bands. For all radiation sources, the presence of gas in the source can serve either as an additional passive gas cell or, in the case of gas discharge lamps, as an active radiation source in bands determined by the molecular structure of the enclosed gas.

Changes and modifications in the specifically described embodiments can be carried out without departing from the principles of the invention which is intended to be limited only by the scope of the appended claims, as interpreted according to the principles of patent law including the doctrine of equivalents.

The embodiments of the invention in which an exclusive property or privilege is claimed are defined as follows:

1. An apparatus for detecting at least one component gas in a sample, comprising:
   source means for providing radiation along at least one optical path in a pre-selected spectral band, said spectral band having at least one absorption line of the component gas to be detected;
   at least one optical detector positioned in said at least one optical path and adapted to detect radiation in said pre-selected spectral band and produce at least one detection output;
   a sample chamber positioned in said at least one optical path between said source and said at least one optical detector and adapted to contain a quantity of sample gas including the component gas to be detected;
   a gas cell enclosing an amount of said component of gas to be detected, fixedly positioned in said at least one optical path in series with said sample chamber; and
   a control including an algorithm for determining a mathematical relationship between said at least one detector output and the concentration of a sample gas filling said sample chamber.

2. The apparatus of claim 1 wherein said source means provides infrared radiation.

3. The apparatus of claim 1 wherein said source means provides ultraviolet radiation.

4. The apparatus of claim 1 further including at least one interference filter positioned in either of said optical paths.

5. The apparatus of claim 1 further including another optical detector reading the radiation energy emitted from said source means in said pre-selected spectral band, said control including a compensation function for correcting errors of said concentration of the sample gas as determined by said algorithm from an output of said another optical detector.

6. The apparatus of claim 5 wherein said compensation function corrects errors caused by fluctuations of the energy radiated from said source means.

7. The apparatus of claim 5 wherein said compensation function corrects errors caused by common mode signals associated with physical phenomena independent of said concentration of the sample gas.

8. The apparatus of claim 7 wherein said physical phenomena includes the temperature of said sample chamber.

9. The apparatus of claim 7 wherein said physical phenomena includes the temperature of said sample gas.

10. The apparatus of claim 7 wherein said physical phenomena includes the pressure of said sample gas.

11. The apparatus of claim 1 for detecting and measuring the concentration of nitrogen-based gases.

12. The apparatus of claim 1 for detecting and measuring the concentration of carbon-based gases.

13. The apparatus of claim 1 for detecting and measuring the concentration of sulfur-based gases.

14. The apparatus of claim 1 wherein said source means encloses at least one gas element present in said sample gas.

15. The apparatus of claim 14 wherein said source means is a gas discharge lamp.

16. The apparatus of claim 1 wherein said at least one optical path comprises first and second optical paths, wherein said at least one optical detector comprises first and second optical detectors positioned respectively in said first and second optical paths and wherein said gas cell is positioned in one of said optical paths.

17. A method for detecting at least one component gas in a sample, comprising:
   providing radiation along at least one optical path in a pre-selected spectral band, said spectral band having at least one absorption line of the component gas to be detected;
   detecting radiation in said at least one optical path in said pre-selected spectral band;
   positioning a sample chamber in said at least one optical path, said sample chamber adapted to contain a quantity of sample gas including the component gas to be detected;
   fixedly positioning at least one gas cell enclosing an amount of said component of gas to be detected in said at least one optical path in series with said sample chamber; and
   determining a mathematical relationship between radiation detected in said at least one optical path and the concentration of a sample gas filling said sample chamber.

18. The method of claim 17 wherein said providing radiation includes providing infrared radiation.

19. The method of claim 17 wherein said providing radiation includes providing ultraviolet radiation.

20. The method of claim 17 further including at least one interference filter positioned in one of said optical paths.

21. The method of claim 17 further including detecting the radiation energy in said pre-selected spectral band along another optical path, and said determining including providing a compensation function for correcting errors of said mathematical relationship from the radiation energy detected along said another optical path.

22. The method of claim 21 wherein said errors are caused by fluctuations of the energy radiated from said source means.

23. The method of claim 21 wherein said errors further include common mode signals associated with physical phenomena independent of the concentration of the gas.

24. The method of claim 23 wherein said physical phenomena includes the temperature of said sample chamber.

25. The method of claim 23 wherein said physical phenomena includes the pressure of said sample gas.

26. The method of claim 17 for detecting and measuring the concentration of nitrogen-based gases.

27. The method of claim 17 for detecting and measuring the concentration of carbon-based gases.

28. The method of claim 17 for detecting and measuring the concentration of sulfur-based gases.

29. The method of claim 17 wherein said source means encloses at least one gas element present in said sample gas.

30. The method of claim 29 wherein said source means is a gas discharge lamp.

31. The method of claim 17 wherein said at least one optical path comprises first and second optical paths, wherein said detecting radiation in said at least one optical path comprises detecting radiation in said first and second optical paths and wherein said fixedly positioning includes fixedly positioning said gas cell in one of said optical paths.

* * * * *

UNITED STATES PATENT AND TRADEMARK OFFICE
CERTIFICATE OF CORRECTION

PATENT NO. : 6,710,347 B1
APPLICATION NO. : 10/096227
DATED : March 23, 2004
INVENTOR(S) : Gideon Eden Page 1 of 1

It is certified that error appears in the above-identified patent and that said Letters Patent is hereby corrected as shown below:

Column 2:
Line 48, "Mi=(Vzg-Vi)/Vz" should be --Mi=(Vzg-Vi)/Vzg--.

Signed and Sealed this

Twenty-fourth Day of August, 2010

David J. Kappos
*Director of the United States Patent and Trademark Office*